United States Patent [19]
Wilson et al.

[11] Patent Number: 5,910,126
[45] Date of Patent: Jun. 8, 1999

[54] PROTECTIVE SUPPORT WRAP FOR EQUINE LIMB

[75] Inventors: Robby W. Wilson, Stephenville; Bryan Kenneth Bray, Granbury; Paul O. Sullivan, Stephenville, all of Tex.

[73] Assignee: Equibrand Corporation, Granbury, Tex.

[21] Appl. No.: 08/924,489

[22] Filed: Aug. 27, 1997

[51] Int. Cl.[6] .................... A61F 13/00; A61F 15/00; A01K 13/00
[52] U.S. Cl. .................... 602/75; 602/62; 119/850
[58] Field of Search .................... 602/23, 27, 62, 602/65, 75; 128/882; 119/850; 54/82

[56] References Cited

U.S. PATENT DOCUMENTS

| | | | |
|---|---|---|---|
| 2,645,222 | 7/1953 | Capossela | 602/65 |
| 3,209,517 | 10/1965 | Hyman | 602/62 |
| 3,504,672 | 4/1970 | Moon | 602/75 |
| 4,140,116 | 2/1979 | Hampicke | 602/62 |
| 4,424,809 | 1/1984 | Yovankin | 602/62 |
| 4,470,411 | 9/1984 | Hoyt, Jr. | 602/62 |
| 4,534,354 | 8/1985 | Bonner, Jr. et al. | 602/75 |
| 4,834,079 | 5/1989 | Benckhuijsen | 602/2 |
| 5,107,827 | 4/1992 | Boyd | 602/62 |
| 5,115,627 | 5/1992 | Scott | 54/82 |
| 5,579,627 | 12/1996 | Vogt | 54/82 |

FOREIGN PATENT DOCUMENTS 2095559  10/1982  United Kingdom .................... 602/75

*Primary Examiner*—Richard J. Apley
*Assistant Examiner*—Denise Pothier
*Attorney, Agent, or Firm*—Akin, Gump, Strauss, Hauer & Feld, L.L.P.

[57] ABSTRACT

A flexible protective support wrap or boot for supporting and protecting the lower leg of a horse, including the fetlock joint, is formed of a panel having a layer of flexible support material, an outer layer of closed loop fabric and an inner layer of woven fabric for contact with the horse's leg. Spaced apart pocket or cup portions are formed in the panel to engage the fetlock joint in overlying relationship to each other when the wrap is secured around the leg. A splint bone protection pad may be secured between and spaced from the side edges and provided with a ridge for locating the pad between the cannon bone and the front deep digital flexor tendon. The entire panel may include a layer of shock absorbing material in addition to the flexible support layer. Multiple spaced apart fastener straps with hook fastener pads are secured to the panel adjacent one side edge for engagement with the loop fabric layer to secure the wrap around the leg in snug fitting relationship.

21 Claims, 4 Drawing Sheets

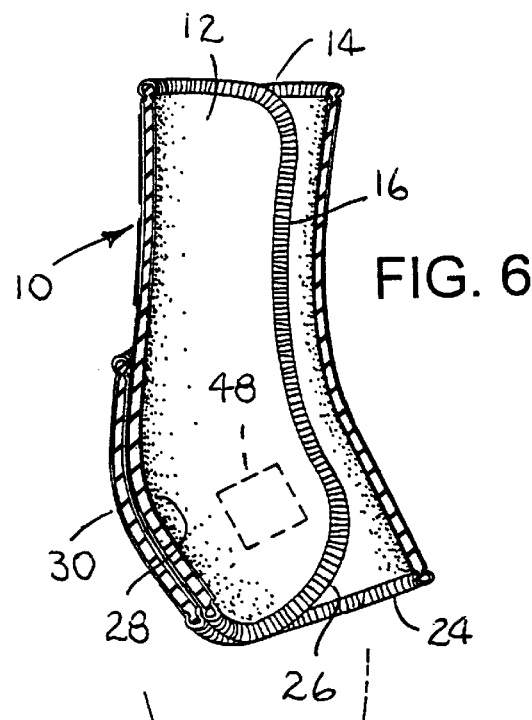
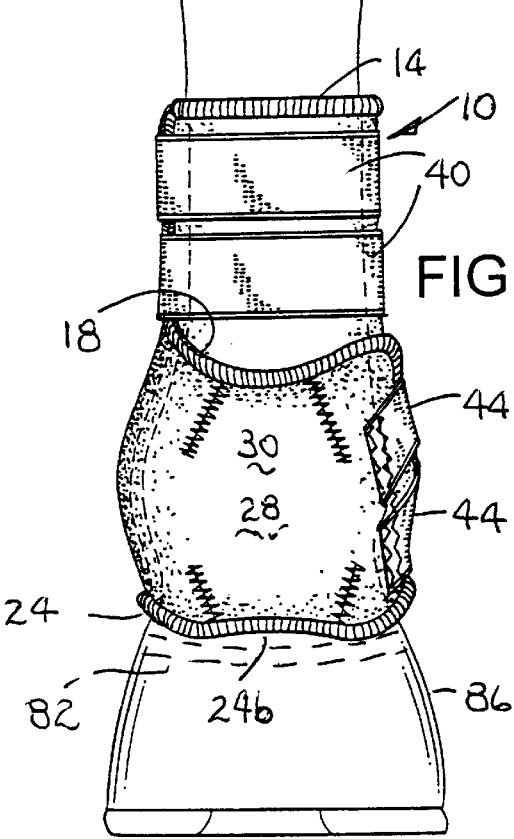
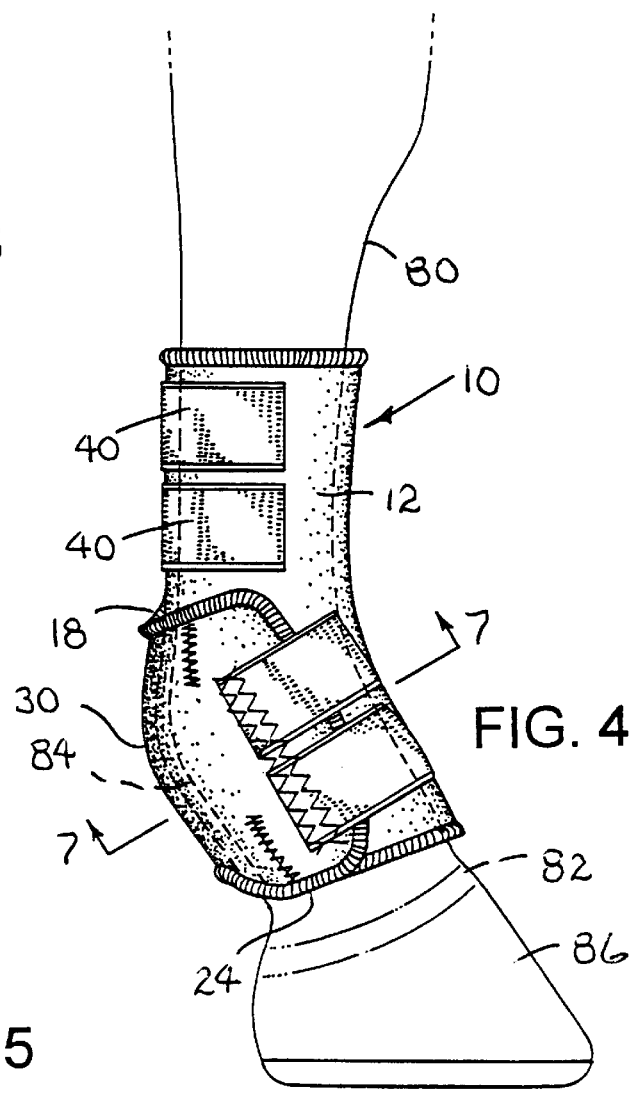
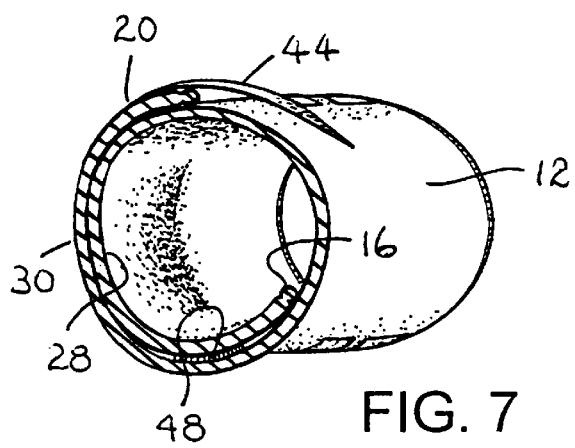

PROTECTIVE SUPPORT WRAP FOR EQUINE LIMB

FIELD OF THE INVENTION

The present invention pertains to a flexible, protective, support wrap or boot for a horse's lower leg including features which facilitate attachment of the wrap to the leg and which provide improved support and protection for the leg and the fetlock.

BACKGROUND OF THE INVENTION

Horses are particularly susceptible to injuries to the lower legs resulting from stress and shock forces incurred during hard running and from external blows due to the horse kicking itself or being kicked by other horses in close proximity, such as during races.

Accordingly, flexible, support boots or wraps have been developed to protect the lower leg area from external blows and to provide support for the tendons, bones and suspensory ligaments. Examples of prior art leg support wraps for horses are disclosed in U.S. Pat. No. 5,115,627 to Scott and 5,579,627 to Vogt.

However, in spite of the prior devices developed, such as disclosed in the Scott and Vogt patents, certain problems have gone unsolved with regard to providing support and protection for equine limbs, such as both the front and rear lower legs of a horse, particularly between the pastern and the knee and including the ligaments, tissues, tendons, the fetlock, fetlock joint and the splint bone. The fetlock joint, in particular, is susceptible to injury during hard running since stress on the joint structure tends to cause the joint to flex sufficiently to overstretch the joint tissues and such that the fetlock will impact the ground.

The construction of prior art support wraps does not provide adequate protection for the fetlock and the fetlock joint. For example, wraps which are provided with laterally extending straps or cradle slings for the fetlock are susceptible to being attached improperly when the wrap is applied to the leg, thus not adequately supporting the fetlock or the leg tendons and tissues. Moreover, the so-called fetlock cradle sling straps of the wraps disclosed in the Scott and Vogt patents do not adequately cover the fetlock and thus do not add additional protection to the fetlock to prevent injury from impact blows or contact with the ground, for example.

Prior art wraps have also been susceptible to rapid wear and deterioration of the cradle sling portions of wraps applied to the rear legs, since the fetlock joints of the rear legs, in particular are likely to make hard and scuffing contact with the ground.

Another problem with prior art support devices pertains to the difficulty with which the wrap or support is attached to the leg and properly positioned on the leg. If the wrap is not properly positioned on the leg, support for the suspensory ligaments, tendons and bone structure is inadequate and, if the wrap is improperly secured, it may become loose and fall off during use. If the wrap is applied too tightly it will be uncomfortable to the horse and may actually be the cause of injury.

Another longstanding problem in the art of protecting and supporting the lower legs of a horse pertains to the tendency for the horse to kick itself in the vicinity of the splint bone of the lower leg. This action typically occurs during turning movements of the horse while it is running and may result in breaking the bone in some instances.

Accordingly, further improvements in support wraps or boots for horses' legs have been sought and have been obtained with the present invention.

SUMMARY OF THE INVENTION

The present invention provides an improved protective support wrap or boot for the lower leg of a horse.

In accordance with one important aspect of the present invention a protective support wrap or boot is provided by a panel of flexible cushioning and uniform support material which is formed to be wrapped around the horse's lower leg and to include a portion forming a first pocket or cup, sometimes referred to as a cradle sling, for placement over the fetlock joint and further wherein the panel includes a portion forming another pocket or cup which is placed over the first pocket when applied to the horse's lower leg to provide additional support and protection for the fetlock and fetlock joint. The panel is preferably formed as a generally rectangular or trapezoidal shaped member with a laterally projecting arm and being further constructed to form the first and second pocket or cup portions.

In accordance with another important aspect of the invention a protective support wrap or boot for a horse's leg is provided which is easy to apply to the leg and includes a flexible panel adapted to be wrapped around the leg, the panel including a first fastener which temporarily fastens the support wrap to the leg so that the person applying the wrap may then grasp the wrap and secure it more easily with additional fastening means, preferably plural straps.

In accordance with another important aspect of the invention a flexible, shock absorbing support wrap or boot for a horse's leg is provided which includes plural pocket or cup portions formed thereon which are adapted to be nested one in the other and disposed over the fetlock joint and further wherein the protective wrap includes plural spaced apart straps for securing the wrap to itself snugly around the leg with minimum risk of the wrap becoming loose or detached from the leg during use. The configuration of the wrap is such as to provide for proper fitting and securement of the wrap to the horse's leg even by inexperienced or untrained persons.

In accordance with a further aspect of the present invention, an improved flexible support wrap or boot is provided which is fabricated of improved materials including an inner layer of a soft, protective fabric, a middle layer of cushioning and tissue support material and an outer layer of closed loop fabric or pile material which is cooperable with securement straps formed of hook fastener material. This combination of material layers provides improved support and comfort when the wrap is applied to a horse's leg and facilitates ease of securing the wrap on the leg with the fastener straps which may be engaged with the outer surface of the panel in any position of the straps so that the wrap may be secured to the horse's leg in a desired well fitted position. Still further, a shock absorbing or impact absorbing layer of material may be added to the inner surface of the wrap to minimize any injury caused by impact blows such as from the horse kicking itself or being kicked by another horse in close proximity.

In accordance with still a further aspect of the present invention, an improved support wrap or boot is provided which includes a unique support pad disposed on the wrap panel and adapted to support and protect the splint bone area of the horse's leg, in particular. An embodiment of the wrap which includes the flexible support panel and extra layers of support and impact absorbing material in the vicinity of the splint bone minimizes the thickness and bulk of the rest of the wrap panel. Moreover, the protective support pad area for the splint bone also includes means forming an elongated ridge in the pad to assist in locating the support wrap and the pad properly on the horse's leg between the back cannon bone and the front deep digital flexor tendon. In this way improved protection and support is provided for the splint bone and associated suspensory ligaments.

In accordance with still a further aspect of the present invention, support wraps or boots for a horse's lower legs, including the rear legs, in particular, is characterized by an abrasion resistant covering over the outer surface of the outer cup or pocket portion of the wrap to minimize wear and deterioration of the wrap as a result of frequent contact with the ground or other running surface which occurs particular at the fetlock of the horse's rear legs.

Those skilled in the art will further appreciate the above-mentioned advantages and superior features of the invention together with other important aspects thereof upon reading the detailed description which follows in conjunction with the drawing.

BRIEF DESCRIPTION OF THE DRAWING

FIG. 4 is an inside elevation of a lower left leg of a horse showing a support wrap or boot in accordance with the invention fitted thereto;

FIG. 5 is a rear elevation of the leg and wrap shown in FIG. 4;

FIG. 6 is a section view taken generally along the line 6—6 of FIG. 5;

FIG. 7 is a section view taken generally along the line 7—7 of FIG. 4;

DESCRIPTION OF PREFERRED EMBODIMENTS

Figure 1:
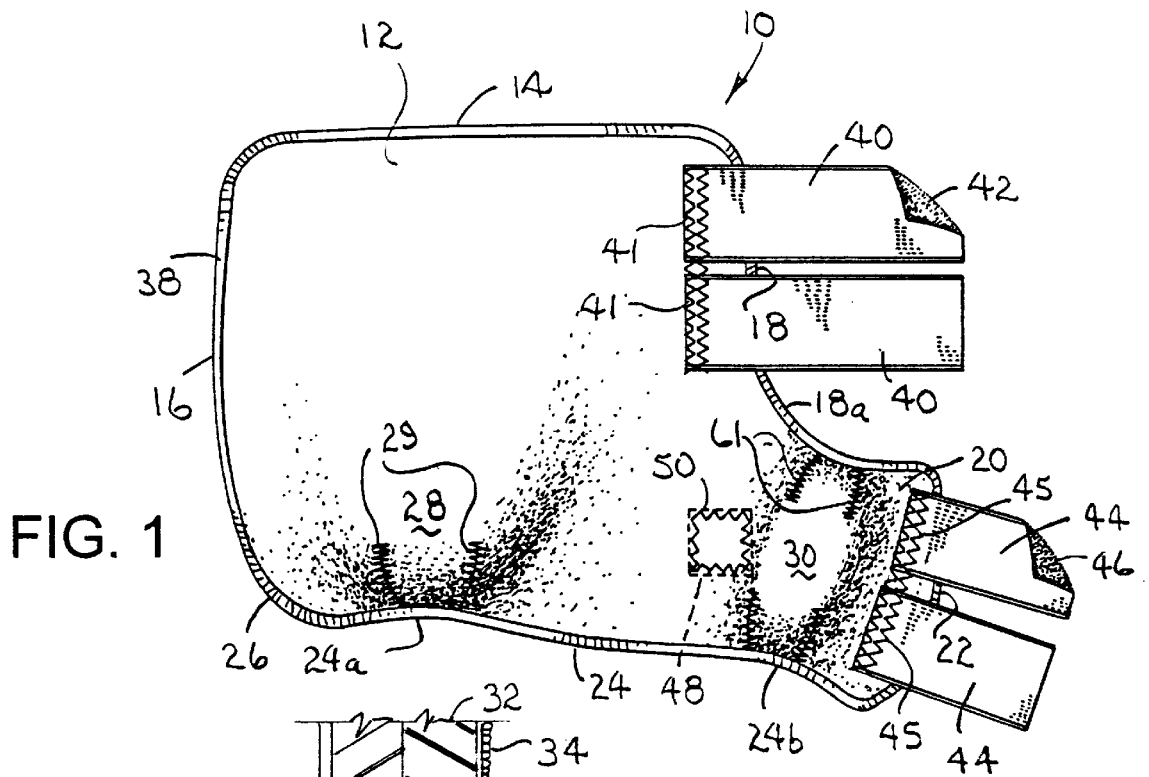
FIG. 1 is an outside plan view of a support wrap or boot of the present invention.

In the description which follows, like parts, portions and areas are marked throughout the specification and drawing with the same reference numerals, respectively. The drawing figures are not necessarily to scale in the interest of clarity and conciseness.

Figure 2:
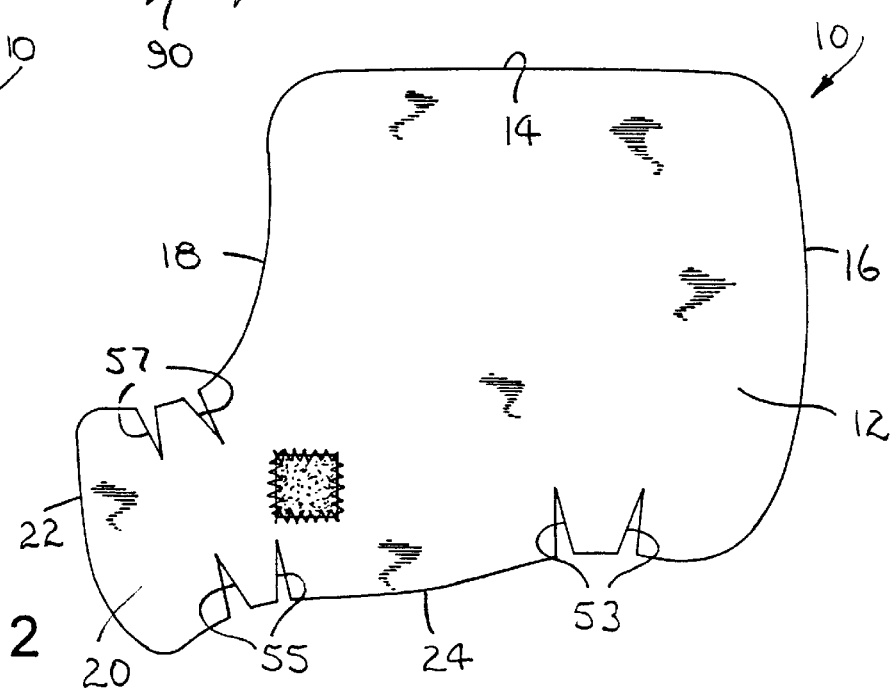
FIG. 2 is a developed plan view of the wrap or boot shown in FIG. 1 prior to finish fabrication to form the protective pocket or cup portions of the wrap.

Referring to FIGS. 1 and 2, a flexible protective support wrap or boot in accordance with the present invention is illustrated and generally designated by the numeral 10.

In FIG. 1, the wrap 10 is shown in an unfolded generally planar or flat position and viewing the outside surface of the boot. The specific wrap 10 illustrated in FIG. 1 is for a horse's left leg. A corresponding boot or wrap for the right leg would be the mirror image of the wrap 10. As shown in FIG. 1, the wrap 10 comprises a panel 12 formed of a composite flexible material to be described in further detail herein. The panel 12 is delimited by a generally straight upper or top edge 14, a first, generally, straight or slightly curved side edge 16 and a second, opposite side edge 18, part of which is concavely curved at 18a between its juncture with the top edge 14 and an arm 20 of the panel. Generous convex curved corner edge portions 17 and 19 interconnect top edge 14 with side edges 16 and 18, respectively. The panel arm 20 has an outer side edge 22 which extends to a bottom edge 24 having a somewhat irregular shape, including two spaced apart concave curved portions 24a and 24b, which may be at least partially formed by a fabrication step to be described in detail herein. Bottom edge 24 is joined to side edge 16 by a convex curved corner portion 26. Unlike the narrow straps or cradle slings of prior art leg wraps, the arm 20 of panel 12 has an overall height which is approximately 40% to 50% of the overall height of the panel 12, defined generally as the distance between edges 14 and 24.

The wrap 10 is advantageously provided with a first sling, pocket or cupped portion 28 formed generally adjacent to bottom edge 24, spaced from side edge 16 and causing the panel 12 to project upwardly out of the plane of the paper when viewing FIG. 1. A second pocket or cupped portion 30 is, preferably, formed in the arm 20 of the panel 12 and also causes the panel to project upwardly out of the plane of the paper when the wrap 10 is arranged flat and viewed in accordance with FIG. 1. The pocket 30 is generally of the same or slightly larger proportions as the pocket 28 and is spaced from the pocket 28 a distance sufficient such that, when the panel 12, including the arm 20 is wrapped around a horse's leg, the pocket 30 will be disposed over the pocket 28 in a somewhat stacked or nesting configuration to provide two layers of the panel 12 in a protective and supportive position for the fetlock joint.

The proportions of the wrap 10 for a medium size horse would require a panel 12 having a height of about eleven inches between edges 14 and 24, a width between side edges 16 and 18 of about eleven inches and a width of the arm 20 of about five inches. The overall dimensions or size of the wrap 10 are dependent on the length of the cannon bone and the horse's weight.

Figures 3, 3A:
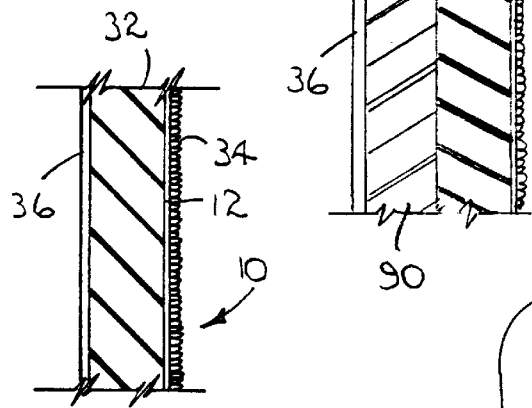
FIG. 3 is a detail section view showing the layers of material forming the wrap panel.
FIG. 3A is a detail section view illustrating multiple layers of material for a support wrap or boot providing maximum support and impact protection.

The wrap 10 is preferably fabricated of a composite layered material wherein a flexible, elastic, supportive layer 32 of neoprene or similar material is provided as a core layer, FIG. 3. The thickness of the layer 32 is preferably about seven millimeters. An outside layer of unbroken loop fabric 34 is bonded to one side of layer 32 and an inside layer of woven nylon lining 36 of about two millimeters thickness is bonded to the opposite side of layer 32, as indicated in FIG. 3. The periphery of the panel 12 may be provided with a suitable serging or stitching 38, as indicated in FIG. 1.

As further shown in FIG. 1, the wrap 10 is provided with fastener means comprising spaced apart elongated flexible straps 40 suitably secured to the outer surface of the panel 12, extending generally parallel to the top edge 14 and extending beyond the side edge 18. The fastener straps 40 are secured to the panel 12 by suitable stitching 41 at a point adjacent to edge 18 but spaced therefrom about twenty-five millimeters to thirty-seven millimeters. The flexible straps 40 are formed of a polymer fabric having hook fastener means 42 formed on the surfaces of the straps opposite the surfaces shown in FIG. 1 so that, as the wrap 10 is secured around the leg of the horse, the straps 40 may be secured to the fabric layer 34 thereby forming cooperating hook and loop fastener means.

A second pair of fastener straps 44 is secured to the arm 20 adjacent and generally normal to the side edge 22 by suitable stitching 45, as indicated in FIG. 1. The straps 44 are preferably formed of the same material as the straps 40 and have hook fastener means 46 formed on the surfaces thereof opposite the surfaces shown in FIG. 1. The straps 40 and 44 are preferably, for a wrap having the other dimensions given herein, of about fifty-one millimeters width. The length of straps 40 is about one hundred fifty millimeters and the length of straps 44 is preferably about one hundred millimeters.

In accordance with an important aspect of the present invention, fastener means in the form of a relatively small pad 48 of hook fastener material is secured to the inside surface of the panel 12, defined by the material layer 36, see FIG. 2 also. The fastener pad 48 is secured to the panel 12 by suitable stitching 50. The fastener pad 48 is preferably disposed adjacent the pocket 30 at the base of the arm 20 at its juncture with the remainder of the panel 12, as shown in FIGS. 1 and 2.

FIG. 2 is also provided to illustrate one preferred manner of fabricating the wrap 10 wherein the laminated, three layer panel 12, prior to attachment of the fastener straps 40 and 44 and binding of the edges with the stitching 38, is fabricated to form the pockets 28 and 30 by cutting elongated somewhat V-shaped notches or darts 53, 55 and 57 in the panel, generally in the areas indicated along the bottom edge 24 and in the arm portion 20, respectively. The darts 53, 55 and 57 preferably have a length of about forty-four millimeters for a wrap 10 having the other dimensions given herein. The pocket portion 28 is formed by gathering the edges of the panel 12 to close the gaps formed by the darts 53, and then applying stitching 29, FIG. 1, to form the pocket or cup portion 28. In like manner, the darts 55 and 57 are closed by stitching 59 and 61, respectively, FIG. 1, to form the pocket or cup portion 30. Only one dart 57 may be necessary, as indicated by the construction of an alternate embodiment described hereinbelow. The fabrication of the wrap 10 is then completed by providing the serging or border stitching 38 followed by attachment of the straps 40 and 44.

Referring to FIGS. 4 through 7, the wrap 10 is illustrated in a working position on a horse's lower left leg 80 between the knee and the cornet band 82. The leg 80 also includes a fetlock 84 and hoof 86. The wrap 10 is taken from an open position, such as illustrated in FIG. 1, and placed on the lower leg 80 just above the cornet band 82 by placing the pocket portion 28 over the fetlock 84 with one hand while wrapping the panel 12 around the leg fairly tightly so that, as the panel arm 20 is brought around the leg, the person applying the wrap can easily judge if the pocket 30 is going to be in an appropriate position disposed over the pocket 28.

When the wrap 10 has been drawn tight enough to achieve this general position of the pocket 30 and with side edge 16 overlapped by the panel 12, the panel is pressed toward itself to cause the fastener pad 48 to engage the outer layer 34 and secure the wrap generally in its working position. At this time, the person applying the wrap 10 to the leg 80 will have both hands free to adjust the position of the wrap and the snugness of the fit of the wrap on the leg 80 by, for example, pulling on the straps 40 while holding the upper portion of the panel 12, adjacent the edge 14, snugly engaged with the leg 80, for example. The straps 40 are then drawn reasonably tight and moderately forcibly engaged with the fabric layer 34 to securely engage the hook fasteners 42 with the loop fabric layer to secure the panel 12 in supportive relationship to the leg 80.

The straps 44 are then secured in their working position shown by being drawn reasonably tight to cause the pocket portion 30 to fit snugly over the pocket portion 28 and the fetlock joint 84. Thanks to the continuous fastener surface provided by the fabric layer 34 the fastener straps 40 and 44 may be secured to the panel 12 in essentially any position of one with respect to the other. The straps 40 are typically wrapped around the leg 80 and spaced apart in horizontal band like positions and the straps 44 are also preferably secured, in generally parallel relation to each other against the outer layer 34 over the entire extent of the straps. Accordingly, the straps 40 and 44 function not only as fastener means but as additional support structure of the wrap 10.

FIGS. 4 through 7 also illustrate an important aspect of the invention wherein, as opposed to providing a relatively narrow elastic strap disposed under the fetlock 84, as in prior art wraps, the wrap panel 12 itself is configured to have an integral portion 20 which is of sufficient height, i.e., about 40% to 50% of the overall height of the panel, which is also configured to form the pocket or cup portion 30 operable to be disposed over the inner pocket or cup 28 in full supportive relationship to the fetlock and to provide additional shock absorbing or cushioning structure to prevent damage to the fetlock during intense exertion or prolonged running by the horse.

Moreover, the provision of the arm 20 with the pocket or cup 30 also assures that this portion of the wrap 10, as well as the pocket 28, is secured to the horse's leg in a proper working position, since it would be clear to a casual observer, as well as an inexperienced person applying the wrap, that the wrap 10 will not fit on the horse's leg with both pocket portions 28 and 30 out of their proper working relationship with respect to the fetlock. Accordingly, even unskilled persons attempting to apply the wrap 10 to the horse's leg will be much more likely to properly position the wrap on the leg. The relatively short, wide, substantially non-elastic fastener straps 40 and 44, also assure that the straps will not be misoriented as they are secured to the outer layer 34 of the panel 12, which could result in loosening of the wrap 10 after it is initially applied to the leg or cause discomfort to the horse. Accordingly, the elasticity or stretchability of the wrap 10 is embodied substantially in the panel 12 and not in the fastener straps 40 and 44.

The construction and use of the wrap 10 is believed to be readily understandable to those of ordinary skill in the art from the foregoing description. As mentioned previously, left and right leg versions of the wrap 10 are preferably fabricated, a left wrap being shown and described in detail herein by way of example only.

Referring briefly to FIG. 3A, the support wrap 10 may be modified to have an additional layer of shock absorbing material applied over the entire area of the panel 12 to provide additional impact blow absorption and protection for the horse's leg. As shown in FIG. 3A, a layer of shock or impact blow absorbing material, generally designated by the numeral 90 may be interposed between the inner layer 36 of woven nylon and the layer 32. A preferred material for the inner layer 90 is vinyl nitrile having a density of about 5–10 pounds per cubic foot. Still further, the elastic flexible support layer 32 may be of a substantially greater thickness than previously described and the layer 90 omitted. However, the combination of the flexible elastic support layer 32 and the impact blow absorbing layer 90 may be advantageous for use with horses which are in early phases of training or are particularly clumsy. The thickness of the material layer 90 may also be approximately five to seven millimeters and the material layer 90 may be secured to the panel 12 by the perimeter stitching 38 together with the material layers 32, 34 and 36.

Figure 8:
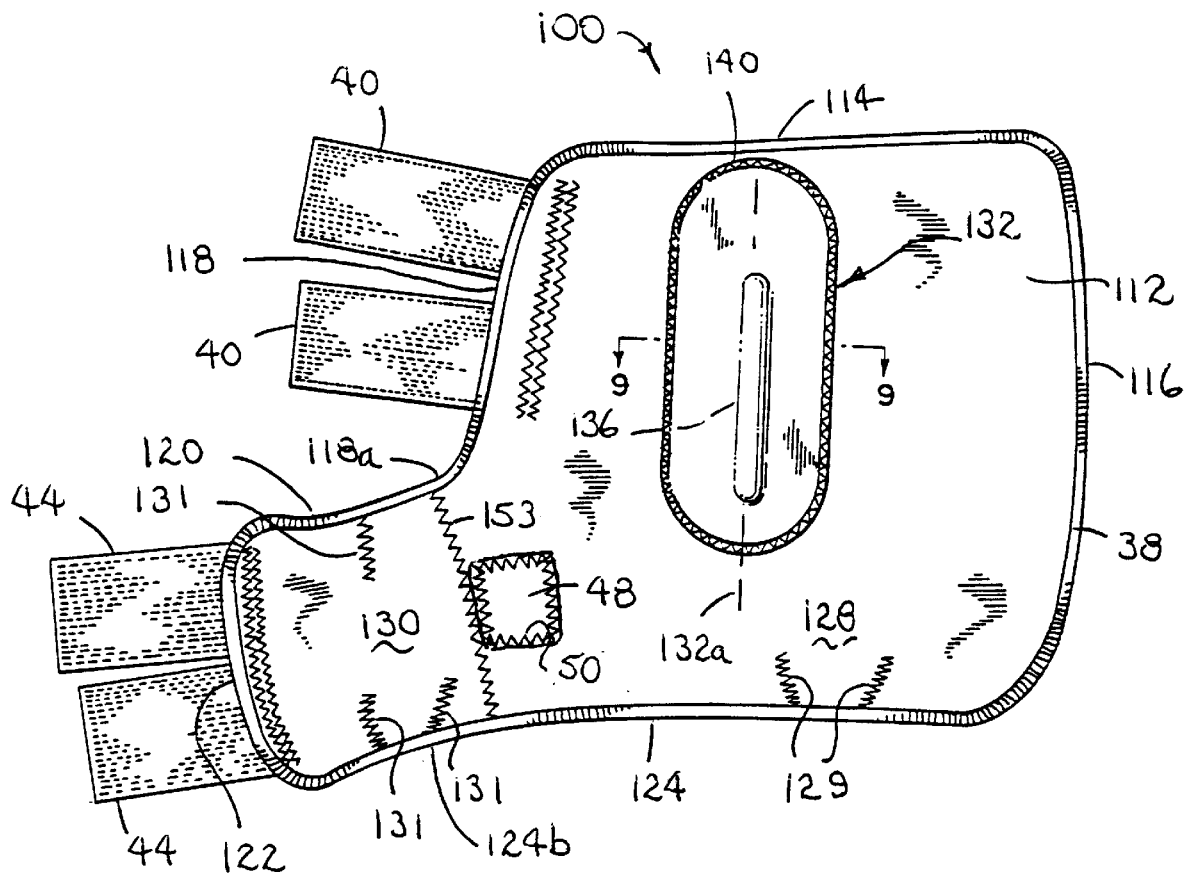
FIG. 8 is an inside plan view of a first alternate embodiment of a protective support wrap or boot in accordance with the invention.

Referring now to FIG. 8, an alternate embodiment of a support wrap or boot in accordance with the present invention is illustrated and generally designated by the numeral 100. The support wrap 100 is of a similar overall shape as compared with the support wrap 10 and is characterized by a flexible panel 112 having a generally straight upper edge 114, a slightly convexly curved side edge 116 and an opposite side edge 118 concavely curved at 118a between its juncture with the top edge 114 and an arm portion 120. The arm 120 has an outer side edge 122 extending to a bottom edge 124 adjacent which are two spaced apart concave pocket or cup portions 128 and 130. The pocket portion 128 is formed by cutting darts in the panel 112 as described above and stitching the V-shaped edges of the darts together at 129. In like manner, the pocket 130 is formed by cutting darts in the material layers forming the panel 112 and stitching the side edges of the darts together by stitching 131. It is noted that only three darts are required to form the pocket 130 as indicated in FIG. 8. Straps 40 and 44 are secured to the panel 112 and the arm 120 in the same manner as for the wrap 10. A fastener pad 48 is suitably secured to the inside surface of panel 112.

Figure 9:
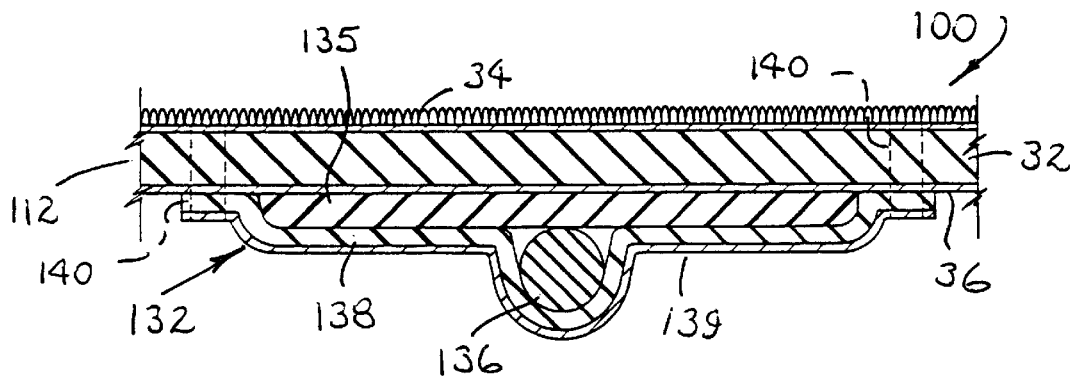
FIG. 9 is a section view taken generally along the line 9—9 of FIG. 8.

Referring also to FIG. 9, an important feature of the wrap 100 is the provision of an additional support and impact blow absorbing and supportive pad, generally designated by the numeral 132, which is preferably secured to the panel 112 on the inside surface thereof and is characterized as a generally oblong or oval shaped portion extending between the top edge 114 and the bottom edge 124 and located approximately 60% of the distance from the side edge 116 to the side edge 118 as regards its longitudinal centerline 132a. The overall width of the pad 132 for a wrap having the dimensions given above is about seventy-five millimeters and the overall length is about 190 millimeters. The top edge of the pad portion 132 is spaced about twenty-five millimeters from the edge 114. As shown in FIG. 9, in particular, the pad portion 132 is formed of a layer of vinyl nitrile shock absorbing material 135 of approximately five to seven millimeters thickness and an elongated generally cylindrical, flexible rod, ridge forming member 136, substantially centered on the pad portion 132 and extending along the centerline 132a. The member 136 forms a ridge which fits between the back cannon bone and the front deep digital flexor tendon of the leg to protect the splint bone and the suspensory ligaments and also to assist in locating the pad portion 132 properly with respect to the horse's leg when the wrap 100 is applied thereto. The member 136 is preferably formed of a flexible elastomeric material, such as natural or synthetic rubber and has a diameter of about ten to fourteen millimeters and a length of about one hundred millimeters. The member 136 is secured in its working position by an inner pad layer 138 overlying the pad layer 135 and preferably formed of the same material as the layer 32. The layer 138 is also of about the same thickness as the material layer 32 and may be secured to the pad member 135 by an adhesive and by stitching around the periphery of the pad portion 132 as indicated at 140.

Figure 10:
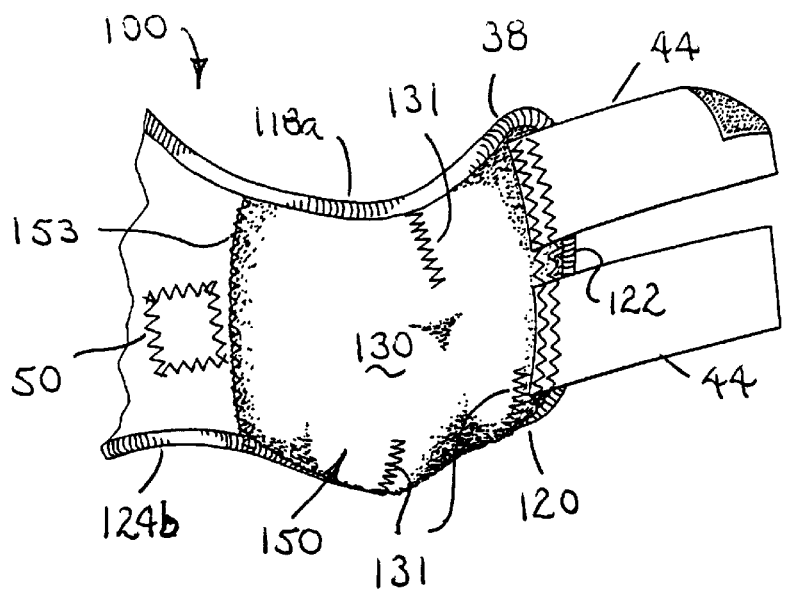
FIG. 10 is a perspective view of a proportion of the support wrap shown in FIG. 8 illustrating a wear resistant pad portion disposed over the outer cup or pocket portion which covers the fetlock joint.
Figure 11:
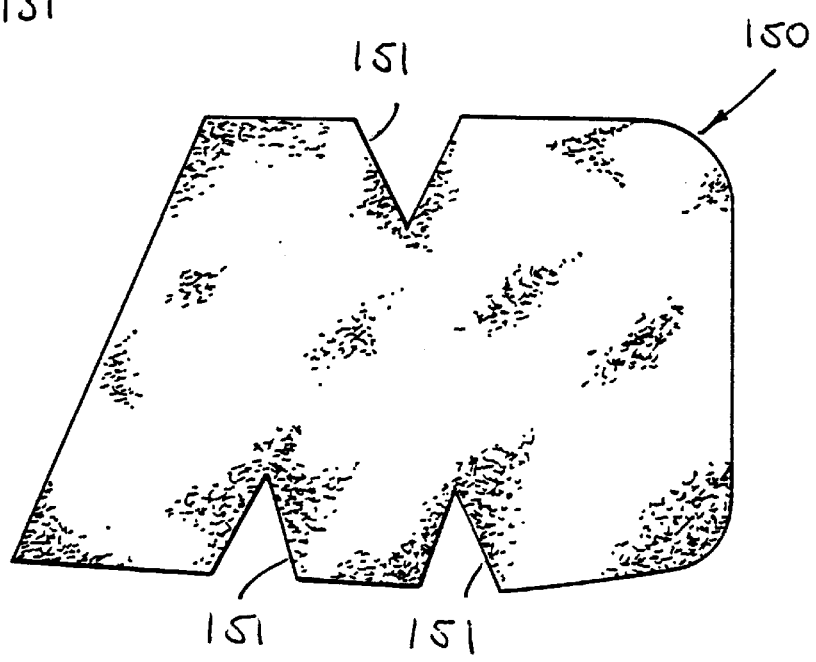
FIG. 11 is a plan view of the wear resistant pad portion showing its general configuration prior to assembly to the support wrap.

Referring now to FIGS. 10 and 11, the wrap 100 is also advantageously provided with an abrasion resistant wear pad 150 disposed over the outer surface of the pocket portion 130 to resist abrasion and rapid wear and tear on the pocket portion when the pocket portion comes into forcible contact with the ground or other running surface on which the horse is traversing.

The wear pad 150 is preferably formed in a somewhat rectangular configuration, as indicated in FIG. 11, with appropriate numbers of darts 151 formed therein so that it may be secured in a working position adjacent the darts cut in the panel 112. As shown in FIG. 10, the wear pad 150 is secured over the outer surface of the pocket portion 130 by suitable stitching 153 and 38 and is also secured in a cup-shaped configuration by the same stitching 131 which forms the pocket portion 130. The material forming the wear pad 150 is preferably an abrasion resistant fabric including Kevlar brand aramid fibers, and sold under the tradename Armortex. With the provision of the wear pad 150 covering the outer surface of the pocket 130, the wrap 100 is particularly advantageous for use on the rear legs of a horse since the fetlock of the rear leg is more likely to come into hard scuffing contact with the ground when the horse is running. However, the wrap 100 may be used on any or all of the legs and a wrap such as the wrap 100 with or without the wear pad 150 may be used to provide additional support for the splint bone thanks to the protective pad portion 132. Thanks also to the provision of the pad portion 132 and its overall configuration, additional support for the tissues and tendons of the horse's leg in the vicinity of the splint bone is provided as well as the additional impact blow absorbing action. In all other respects, the wrap 100 may be substantially like the wrap 10 including the provision of the attachment or fastener pad 48, the peripheral stitching 38 and a configuration wherein the material layers provided for the panel 112 are substantially like those shown in FIGS. 3 or 3A.

However, since the splint bone area is the most sensitive and likely to incur damaging impact blows, a wrap such as the wrap 100 provides the added impact blow resisting or absorbing pad portion 132 in the most susceptible area and therefore eliminates the requirement for additional impact blow resisting material in areas which are not likely to be susceptible to impact blows. Thus, the overall thickness of the wrap 100 is such as to make the wrap less bulky.

Although preferred embodiments of the invention have been described in detail, those skilled in the art will recognize that various substitutions and modifications may be made to the invention without departing from the scope and spirit of the appended claims.

What is claimed is:

1. A protective support wrap for a lower leg of a horse comprising:

a flexible panel formed of a first layer of substantially flexible shock absorbing material having a top edge, a bottom edge and spaced apart side edges, said panel including a portion forming a first pocket generally adjacent said bottom edge and a portion of said panel forming a second pocket spaced from said first pocket sufficiently such that, upon wrapping said panel around a lower leg of a horse adjacent a fetlock joint of the lower leg, said first pocket covers the fetlock joint and said second pocket is engaged with said first pocket in nesting relationship whereby the fetlock joint by during use at said first pocket and said second pocket to provide two thicknesses of said first layer covering the fetlock joint to protect and support the fetlock joint.

2. The support wrap set forth in claim 1 wherein:

said second pocket is formed in a laterally extending arm of said panel.

3. The support wrap set forth in claim 1 including:
fastener means disposed adjacent one of said side edges for securing said wrap around the leg.

4. The support wrap set forth in claim 3 wherein:
said fastener means comprises at least one fastener strap extending from one of said side edges.

5. The support wrap set forth in claim 4 wherein:
said fastener means includes two, spaced apart fastener straps secured to said panel adjacent one of said side edges.

6. The support wrap set forth in claim 5 wherein:
said fastener means includes two, spaced apart, generally parallel fastener straps secured to said panel adjacent said second pocket.

7. The support wrap set forth in claim 4 wherein:
said fastener means includes at least one fastener strap secured to said panel adjacent said second pocket.

8. The support wrap set forth in claim 1 including:
fastener means comprising spaced apart laterally extending straps connected to said panel adjacent one of said side edges, said straps including hook fastener means formed thereon, and said panel including cooperating loop fastener means forming at least part of an outer layer of said panel.

9. The support wrap set forth in claim 1 wherein:
said panel includes a second layer secured to said first layer on one side thereof and forming fastener means for said wrap.

10. The support wrap set forth in claim 9 wherein:
said panel includes a third layer secured to said first layer on a side of said first layer opposite said second layer and comprising a protective sheet for contact with the leg.

11. The support wrap set forth in claim 1 including:
an impact blow absorbing pad portion secured to said panel between said top edge and said bottom edge and spaced from side edges, respectively, said pad portion being located on said panel such as to provide impact blow protection to a splint bone of the leg.

12. The support wrap set forth in claim 11 wherein:
said pad portion includes a first layer of impact blow absorbing material, and means forming an elongated ridge portion for disposition between a cannon bone and a tendon of the leg for locating said pad portion over suspensory ligaments and the splint bone for support and protection thereof.

13. The support wrap set forth in claim 12 wherein:
said pad portion includes a layer of material disposed over said means forming said ridge and forming an inner layer for contact with the leg when said support wrap is applied thereto.

14. The support wrap set forth in claim 1 including:
a wear pad secured to an outer surface of said panel substantially over said second pocket.

15. The support wrap set forth in claim 1 wherein:
said panel includes fastener means secured to a surface of said panel between said edges and operable to engage a surface of said panel when wrapped around the leg to position said panel initially upon wrapping said panel around leg until additional fastener means on said panel can be secured to retain said panel wrapped around the leg.

16. A protective support wrap for a lower leg of a horse comprising:
a panel formed of a first layer of flexible material, a second outer layer secured to one side of said first layer and forming one part of fastener means for said wrap and a third inner layer secured to an opposite side of said first layer and forming a contact surface for engagement with a leg of a horse;
said panel including a top edge, a bottom edge and spaced apart side edges, a first pocket portion of said panel formed adjacent said bottom edge and a second pocket portion of said panel spaced from said first pocket portion a sufficient distance such as to engage said first pocket portion in nesting relationship when said wrap is applied to the leg; and
spaced apart fastener straps secured to said panel adjacent one of said side edges, at least one fastener strap secured to said panel adjacent said one side edge and at least one fastener strap secured to said panel adjacent said second pocket portion and operable to be engaged with said outer layer to secure said wrap around the leg with said pocket portions disposed adjacent a fetlock joint of the leg.

17. A protective support wrap for a lower leg of a horse comprising:
a panel formed of a first layer of flexible material comprising neoprene having a thickness of about five millimeters to seven millimeters, a second outer layer secured to one side of said first layer and forming one part of fastener means for said wrap and a third inner layer secured to an opposite side of said first layer and forming a contact surface for engagement with a leg of a horse;
said panel including a top edge, a bottom edge and spaced apart side edges, a first pocket portion of said panel formed adjacent said bottom edge and a second pocket portion of said panel spaced from said first pocket portion a sufficient distance such as to engage said first pocket portion in nesting relationship when said wrap is applied to said leg; and
spaced apart fastener straps secured to said panel adjacent one of said side edges and operable to be engaged with said outer layer to secure said wrap around the leg with said pocket portions disposed adjacent a fetlock joint of the leg.

18. A protective support wrap for a lower leg of a horse comprising:
a panel formed of a first layer of flexible material, a second outer layer secured to one side of said first layer and forming one part of fastener means for said wrap and a third inner layer secured to an opposite side of said first layer and forming a contact surface for engagement with a leg of a horse;
said panel including a top edge, a bottom edge and spaced apart side edges, a first pocket portion of said panel formed adjacent said bottom edge and a second pocket portion of said panel spaced from said first pocket portion a sufficient distance such as to engage said first pocket portion in nesting relationship when said wrap is applied to the leg;
spaced apart fastener straps secured to said panel adjacent one of said side edges and operable to be engaged with said outer layer to secure said wrap around the leg with said pocket portions disposed adjacent a fetlock joint of the leg; and
fastener means secured to said inner layer of said panel between said side edges and operable to engage said outer layer when said panel is wrapped around the leg to position said panel initially so that said fastener straps may be secured to said outer layer with said pocket portions disposed in protective relationship to the fetlock joint.

19. A protective wrap for a lower leg of a horse comprising:

a panel formed of a first layer of substantially flexible shock absorbing material having a top edge, a bottom edge and spaced apart side edges, said panel including an arm portion projecting from one of said side edges and having a height of about forty percent to fifty percent of the overall height of said panel between said top edge and said bottom edge, said panel being of sufficient width between said side edges to provide for wrapping said panel completely around a leg of a horse such that said panel overlies the fetlock joint, said side edges overlap each other and said arm portion of said panel overlies another portion of said panel and the fetlock joint, said panel is formed with first and second pockets spaced apart from each other, one of said pockets being formed in said arm portion of said panel, said pockets being spaced apart from each other sufficiently to provide for said pocket in said arm portion being engaged with the other pocket in nesting relationship when said wrap is disposed around the leg to provide two thicknesses of said first layer disposed in protective covering of the fetlock joint; and fastener means on said panel adjacent one of said side edges and said arm portion for securing said panel snugly around the leg with said two thicknesses of said first layer substantially covering the fetlock joint to absorb impact blows against the fetlock joint.

20. The support wrap set forth in claim 19 wherein:

said fastener means include two spaced apart fastener straps secured to said panel adjacent one of said side edges and two spaced apart fastener straps secured to said panel at said arm portion.

21. The support wrap set forth in claim 20 wherein:

said fastener straps include hook fastener portions formed thereon and said panel includes a layer of loop material secured to said layer of flexible shock absorbing material for engaging said hook fastener portions of said straps to provide for fastening said wrap to said leg.

* * * * *

UNITED STATES PATENT AND TRADEMARK OFFICE
CERTIFICATE OF CORRECTION

PATENT NO.   : 5,910,126  
DATED        : June 6, 1999  
INVENTOR(S)  : Wilson et al.

It is certified that error appears in the above-identified patent and that said Letters Patent is hereby corrected as shown below:

<u>Column 8,</u>  
Line 61, after "whereby the fetlock joint", delete "by during use at" and replace with -- is covered by said panel at said --.

Signed and Sealed this

Fifth Day of August, 2003

JAMES E. ROGAN  
*Director of the United States Patent and Trademark Office*